US006900026B2

(12) United States Patent
Wallace et al.

(10) Patent No.: US 6,900,026 B2
(45) Date of Patent: May 31, 2005

(54) METHODS FOR IDENTIFYING COMPOUNDS AS ANTIOXIDANTS

(75) Inventors: Douglas C. Wallace, Atlanta, GA (US); Simon Melov, Atlanta, GA (US); James D. Crapo, Cherry Hills Village, CO (US); Brian J. Day, Englewood, CO (US)

(73) Assignees: Duke University, Durham, NC (US); Emory University, Atlanta, GA (US)

( * ) Notice: Subject to any disclaimer, the term of this patent is extended or adjusted under 35 U.S.C. 154(b) by 116 days.

(21) Appl. No.: 10/039,869

(22) Filed: Nov. 9, 2001

(65) Prior Publication Data

US 2003/0167474 A1 Sep. 4, 2003

Related U.S. Application Data

(63) Continuation of application No. 09/454,126, filed on Dec. 3, 1999, now abandoned, which is a continuation of application No. 08/924,301, filed on Sep. 5, 1997, now abandoned.
(60) Provisional application No. 60/024,702, filed on Sep. 6, 1996.

(51) Int. Cl.$^7$ .............................................. C12Q 1/34
(52) U.S. Cl. ......................................... 435/18; 424/9.2
(58) Field of Search ............................ 435/4, 18, 69.2; 424/9.1, 9.2; 514/185; 800/18

(56) References Cited

U.S. PATENT DOCUMENTS 5,403,834 A  4/1995 Malfroy-Camine et al. . 514/185

FOREIGN PATENT DOCUMENTS

WO  95/14769  11/1993  ............ C12N/5/00

OTHER PUBLICATIONS

Li, Y. Dilated Cardiomyopathy and Neonatal Lethality in Mutant Mice Lacking MnSOD. Nature Genetics vol. 11, Dec. 1995, 376–381.*
Baker et al. (1998) "Synthetic Combined Superoxide Dismutase/Catalase Mimetics are Protective as a Delayed Treatment in a Rat Stroke Model: A Key Role for Reactive Oxygen Species in Ischemic Brain Injury" *The Journal of Pharmacology and Experimental Therapeutics* 284:215–221.
Chan et al. (1996) "Studies of Neuronal Injury Mechanism in Focal Stroke Using Mitochondrial Manganese Superoxide Dismutase–Deficient Mice" *6$^{th}$ Int. Symp. Pharmacology of Cerabral Ischemia* pp. 573–579.
Beal, M.F. (1995) "Aging, Energy and Oxidative Stress in Neurodegenerative Diseases" *Ann. of Neurol.* 38:357–366.
Carlsson et al. (1995) "Mice Lacking Extracellular Superoxide Dismutase are More Sensitive to Hyperoxia" *Proc. Natl. Acad. Sci. USA* 92:6264–6268.
Chan et al. (1995) "Transgenic Mice and Knockout Mutants in the Study of Oxidative Stress in Brain Injury" *J. of Neurotrauma* 12:815–824.

Chan et al. (1995) "Transgenic Mice and Knockout Mutants in the Study of Oxidative Stress in Brain Injury" *J. of Neurotrauma* 12:815–824.
Day et al. (1995) "A Metalloporphyrin Superoxide Dismutase Mimetic Protects Against Paraquat–Induced Endothelial Cell Injury, in vitro" *J. of Pharm. and Experimental Therapeutics* 275:1227–1232.
Day, B.J. and Crapo, J.D. (1996) "A Metalloporphyrin Superoxide Dismutase Mimetic Protects Against Paraquat–Induced Lung Injury in vivo" *Toxicology and Applied Pharmacology* 140:94–100.
Doctrow et al. (1997) "Salen–Manganese Complexes: Combined Superoxide Dismutase/Catalase Mimics with Broad Pharmacological Efficacy" *Advances in Pharmacology* 38:247–268.
Friedlander et al. (1997) "Inhibition of ICE Slows ALS in Mice" *Nature* 388:31.
Halliwell, B. (1992) "Reactive Oxygen Species and the Central Nervous System" *J. of Neurochem.* 59:1609–1623.
Ikonomidou, C. (1996) "Motor Neuron Degeneration Induced by Excitotoxin Agonists has Features in Common with Those Seen in the SOD–1 Transgenic Mouse Model of Amyotrophic Lateral Sclerosis" *J. of Neuropathol. Exp. Neurol.* 55:211–224.
Kostic et al. (1997) "Prolonging Life in a Transgenic Mouse Model of Familial Amyotrophic Lateral Sclerosis" *Science* 227:559–562.
Lebovitz et al. (1996) "Neurodegeneration, Myocardial Injury, and Perinatal Death in Mitochondrial Superoxide Dismutase–Deficient Mice" *Proc. Natl. Acad. Sci. USA* 93:9782–9787.
Li et al. (1995) "Dilated Cardiomyopathy and Neonatal Lethality in Mutant Mice Lacking Manganese Superoxide Dismutase" *Nature Genetics* 11:376–381.
Mattson, M.P. "Calcium and Neuronal Injury in Alzheimer's Disease" *Ann. NY Acad. of Sciences* 747:50–76, no date avail.

(Continued)

Primary Examiner—Ralph Gitomer
(74) Attorney, Agent, or Firm—Greenlee, Winner and Sullivan, P.C.

(57) ABSTRACT

The present application describes methods for the testing of compounds of potential usefulness as therapeutic antioxidants and/or as therapeutic free radical scavengers. The animal model for testing such compounds is the Sod2CJE homozygous Manganese Superoxide Dismutase-deficient mouse. When pups of these mice are treated with certain antioxidants, they survive past about 7 days of age, and later develop characteristic histological changes and characteristic neurobehavioral disorders. Those treated mice can be further treated with test compounds which may or may not cross the blood brain barrier, and the life span and physical and neurobehavioral characteristics of those mice provide information about the potential utility of the test compound as a therapeutic antioxidant. Phenotypes of the treated mice allow conclusions regarding targeted areas of the brain and thus, applications to particular disorders such as Parkinsonism.

3 Claims, 11 Drawing Sheets

OTHER PUBLICATIONS

Melov et al. (1997) "Multi–Organ Characterization of Mitochondrial Genomic Rearrangement in ad libitum and Caloric Restricted Mice Show Striking Somatic Mitochondrial DNA Rearrangements with Age" *Nucleic Acids Research* 25:974–982.

Pecoraco et al. (1994) "Interaction of Manganese with Dioxygen and Its Reduced Derivatives" *Chem. Rev.* 94:807–826.

Reaume et al. (1996) "Motor Neurons in Cu/Zn Superoxide Dismutase–Deficient Mice Develop Normally but Exhibit Enhanced Cell Death After Axonal Injury" *Nature Genetics* 13:43–47.

Simonian and Coyle (1996) "Oxidative Stress in Neurodegenerative Diseases" *Annu. Rev. Pharmacol. Toxicol.* 36:83–106.

Szabo, C. (1996) "Physiological and Pathophysiological Roles of Nitric Oxide in the Central Nervous System" *Brain Res. Bul.* 41:131–141.

Wallace, D.C. (1996) "Mitochondrial DNA Mutations and Bioenergetic Defects in Aging and Degenerative Diseases" *Mitochondrial Disorders,* eds. D.N. Rosenburg et al., pp. 237–269.

Wang et al. (1996) "Superoxide Dismutase Protects Calcineurin from Inactivation" *Nature* 383:434–437.

Yim et al. (1996) "A Gain–of–Function of an Amyotrophic Lateral Sclerosis–Associated Cu, Zn–Superoxide Dismutase Mutant: An Enhancement of Free Radical Formation Due to a Decrease in Km for Hydrogen Peroxide" *Proc. Natl. Acad. Sci. USA* 93:5709–5714.

* cited by examiner n=66
Gehan's Wilcoxon test: P=0.007
Uncensored=
Censored=7
Unrestricted Litter size=32
Restricted litter size=32

35 day old SOD2+/+ Euk 8

35 day old SOD2−/− Euk 8

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 1 cgagggcat ctagtggaga ag        22

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
cacacatcgg gaaaatggtt t                                              21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
ttagggctca ggtttgtcca gaa                                            23
```

METHODS FOR IDENTIFYING COMPOUNDS AS ANTIOXIDANTS

CROSS-REFERENCE TO RELATED APPLICATIONS

This application is a Continuation of U.S. application Ser. No. 09/454,126 filed Dec. 3, 1999 now abandoned, which is a Continuation of U.S. application Ser. No. 08/924,301 filed Sep. 5, 1997 now abandoned, which is a Continuation-in-Part of U.S. Provisional Patent Application Ser. No. 60/024,702, filed Sep. 6, 1996.

ACKNOWLEDGEMENT OF FEDERAL RESEARCH SUPPORT

This invention was made, at least in part, with funding from the National Institutes of Health. Accordingly, the United States Government may have certain rights in this invention.

BACKGROUND OF THE INVENTION

The field of the invention is the area of the testing of pharmaceuticals in animal model systems, particularly those pharmaceuticals of benefit in protecting a human or animal against oxidative damage.

Oxygen is a critical element in biological systems, having roles including a terminal electron acceptor in oxidative phosphorylation, in dioxygenase reactions, in hydroxylation reactions, in reactions involving activation and/or inactivation of xenobiotics, including carcinogens and in normal animal host defense mechanisms. Despite the wide range of essential and desirable reactions in which oxygen plays a role, the generation of excess amounts of oxygen free radicals through cellular processes has deleterious effects on biological systems including, without limitation, membrane lipid peroxidation, oxidation of nucleic acids, oxidation of sulfhydryl bonds and other moieties which are sensitive to oxidative damage. It has also been theorized that the effects of aging are due, in part, to cumulative oxidative damage to cellular systems.

Biological antioxidants include enzymes such as superoxide dismutase, catalase, selenium glutathione peroxidase and phospholipid glutathione peroxidase and compounds including tocopherols, tocotrienols, carotenoids, quinones, bilirubin, ascorbic acid, uric acid, ovothiols and certain metal binding proteins.

Oxygen free radicals in biological systems include superoxide anion ($\cdot O_2{}^{2-}$). Sequential univalent reactions of the superoxide radical yield hydrogen peroxide, hydroxyl radical, and water. Catalase converts hydrogen peroxide to water and molecular oxygen.

Oxygen radical injury has been implicated in pulmonary oxygen toxicity, adult respiratory distress syndrome, bronchopulmonary dysplasia, sepsis syndrome, amyotrophic lateral sclerosis, and various ischemia-reperfusion syndromes including myocardial infarction, stroke, cardiopulmonary bypass, organ transplantation, necrotizing enterocolitis, acute renal tubular necrosis, mitochondrial disease, Alzheimer's disease, and Parkinson's disease among others. Accumulated free radical damage has also been associated with the normal aging process.

SUMMARY OF THE INVENTION

The present invention provides a method for testing compounds of potential pharmaceutical use in protecting against the oxidative damage associated with free radicals in an animal model system. This animal model is the mouse in which the mitochondrial gene (Sod2) encoding manganese superoxide dismutase (MnSOD) has been inactivated. The preferred animal model for use in the present invention is the homozygous MnSOD-deficient (Sod2CJE) mouse described in Li et al. (1995) Nat. Genet. 11, 376–381. Use of this animal model also allows the distinction between potentially therapeutic compounds which do cross the blood-brain barrier from those which do not cross the blood-brain barrier. Those anti-oxidant compounds which do not cross the blood-brain barrier prolong the survival of the homozygous MnSOD-deficient mice but do not prevent the development of overt neurological symptoms. Those compounds which cross the blood-brain barrier prolong the survival of the homozygous MnSOD-deficient mice and also prevent or delay the onset of the symptoms of neurological damage resulting from free radical damage at the level of the central nervous system.

The present method comprises the step of administering a potentially therapeutic antioxidant compound to a homozygous mutant mouse, monitoring survival in comparison to an untreated (control) homozygous MnSOD-deficient mouse population, monitoring the controls and the treated mice for symptoms of central nervous system damage, and identifying compounds of potential use in antioxidant therapy as those which prolong survival and/or which delay or prevent symptoms of oxidative damage to the central nervous system.

The present invention also provides a method for the testing of compounds which are of use in preventing or reducing oxidative damage, for example, damage resulting from free radicals, in the central nervous system. Such potentially useful compounds are identified as preventing, delaying or reducing overt symptoms of nervous system damage in the homozygous transgenic MnSOD-deficient mouse. Desirably the mouse is the Sod2CJE(−/−) mouse described by Li et al. (1995) Nature Genetics 11, 376–381. Additionally, the present animal model system and methods can be used to identify compounds of use in treating or preventing oxidative damage in medical conditions including, but not limited to, mitochondrial disease, lupus, Crohn's disease, gastric ulcers, oxygen toxicity, burns, renal failure associated with organ transplantation, herpes simplex infection, osteoarthritis, intestinal ischemia, stroke, myocardial infarction, amyotrophic lateral sclerosis (ALS) or Lou Gehrig's disease, and Alzheimer's disease. Compounds useful for preventing or delaying certain manifestations of aging can also are identified by the present methods, especially those manifestations of the aging process, which are the result of free radical damage.

which have been treated with the SOD mimetic MnTBAP as described hereinbelow or untreated (controls). For the data shown, the litter size has not been restricted; as noted above, the typically unrestricted litter size was about 12 pups. As above, survival is greatly enhanced by MnTBAP treatment.

Figure 3:
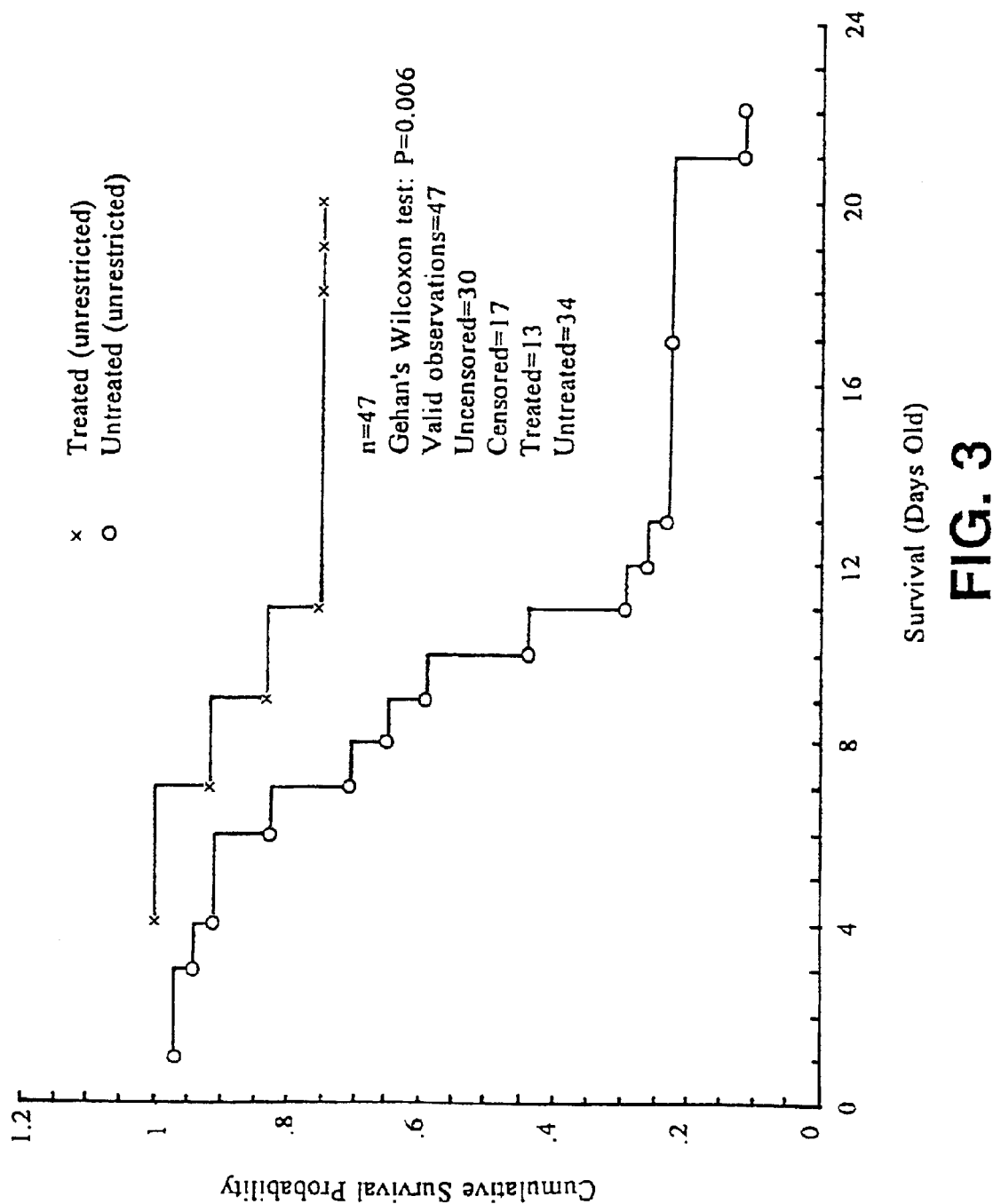

FIG. 3 illustrates the cumulative survival probability over time for Sod2CJE(−/−) mice in which litter size was restricted to six or fewer pups. Untreated animals received no potential antioxidant or free radical scavenging compounds while treated animals received MnTBAP as described in the Examples. As for litters which have not been restricted in size, MnTBAP treatment significantly prolongs the survival of the MnSOD knockout mice.

Figure 4:
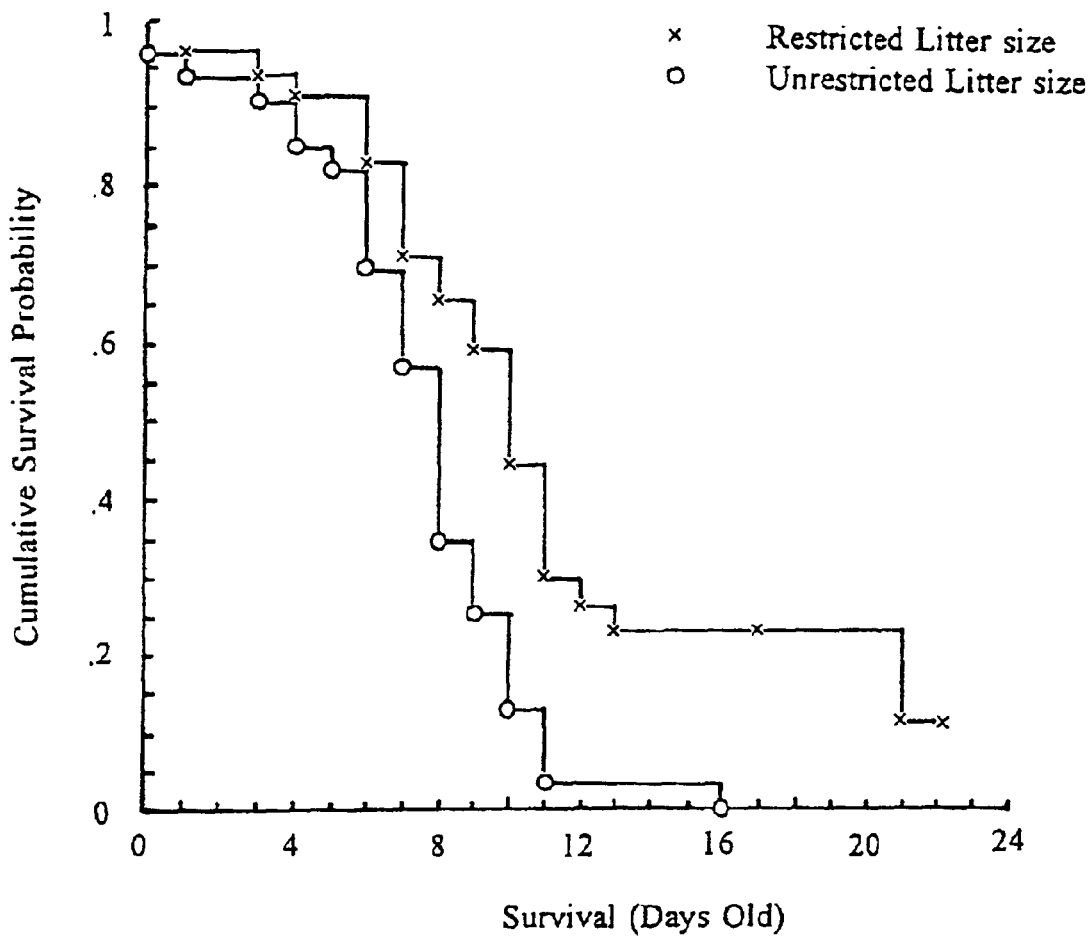

FIG. 4 provides a graphical representation of survival probability over time for untreated Sod2CJE(−/−) mice where the litter size was restricted to 6 or fewer animals or where the litter size was unrestricted (typical unrestricted litter size was about 12 pups). This graph shows that there is a small increase in survival probability for the MnSOD knockout mice in litters of restricted size, presumably due to less stress.

Figure 5B:
Figure 5A:
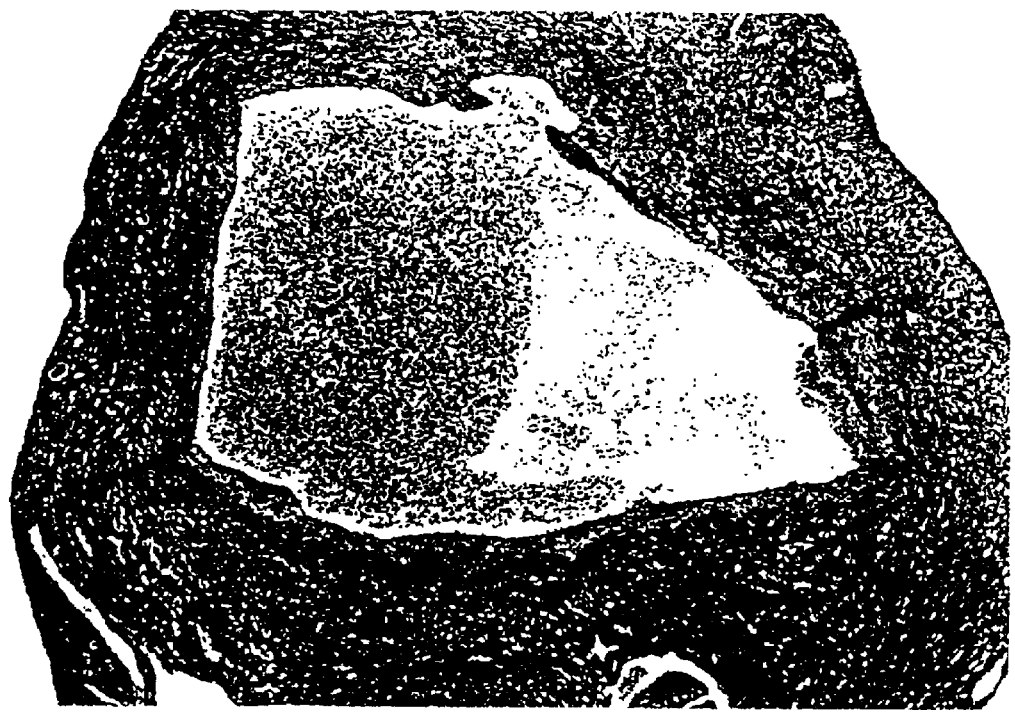
Figure 5C:
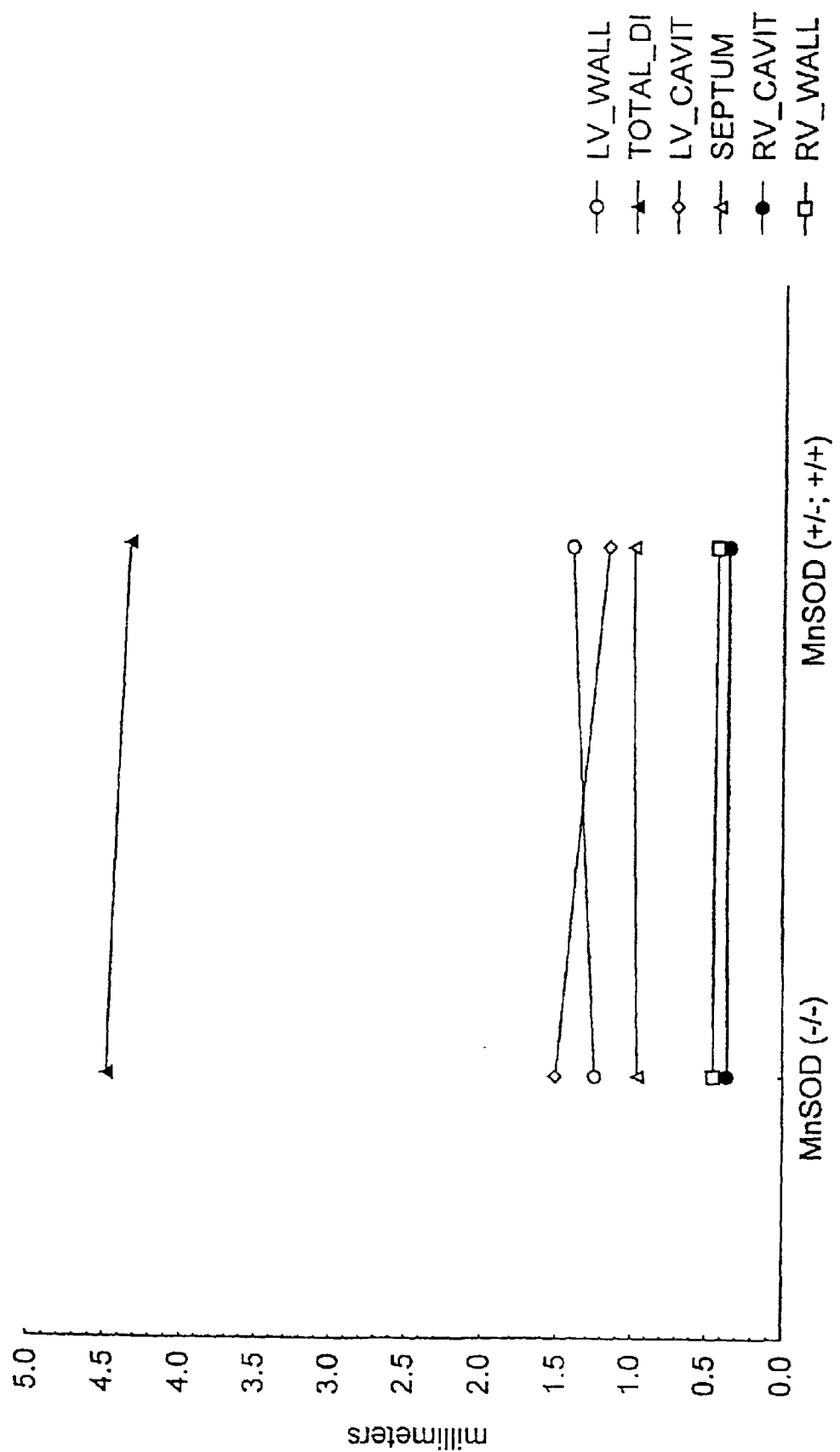

FIGS. 5A–5C are photographs of a hematoxylin and eosin stained cross sections of hearts from untreated 6 day old Sod2CJE(−/−) and (+/+) mice showing marked dilated cardiomyopathy of the left ventricle in the Sod2CJE(−/−) mouse. FIG. 5A is from an untreated Sod2CJE(−/−), FIG. 5B is from an untreated Sod2CJE(+/+) and FIG. 5C is a plot of means of cardiac parameters of treated Sod2CJE(−/−) animals from 20–21 days of age (n=14) versus treated 21 day old Sod2CJE(+/−) and Sod2 (+/+) (n=7) animals showing no significant difference between the mutant and normal animals (0.1<P<1).

Figure 6A:
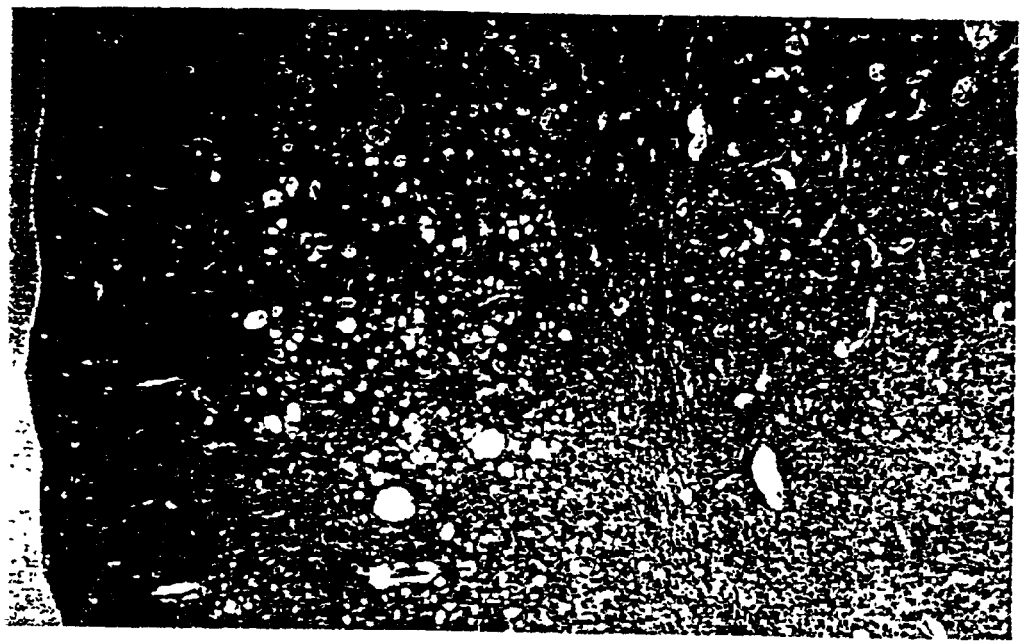
Figure 6B:
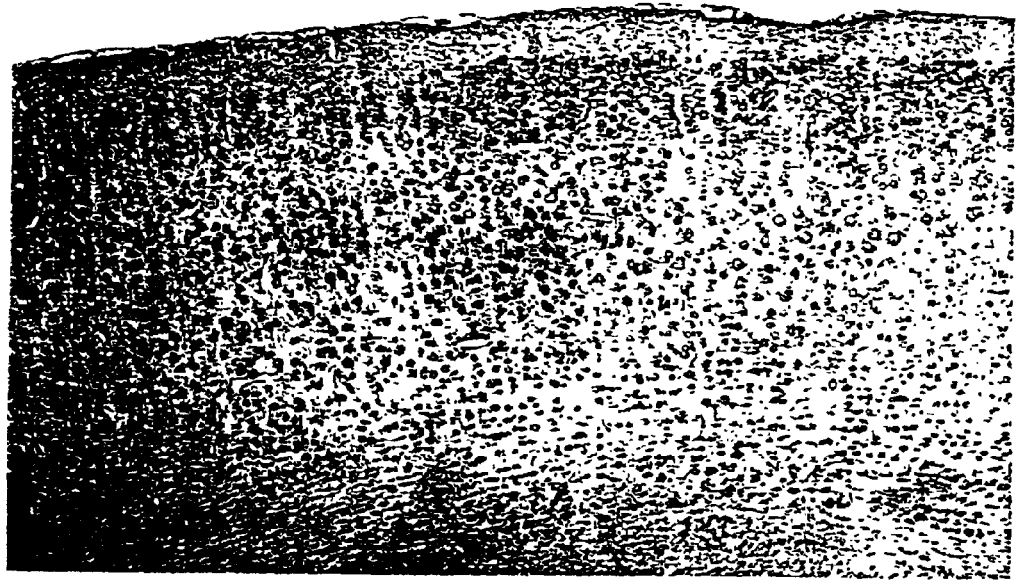
Figure 6C:
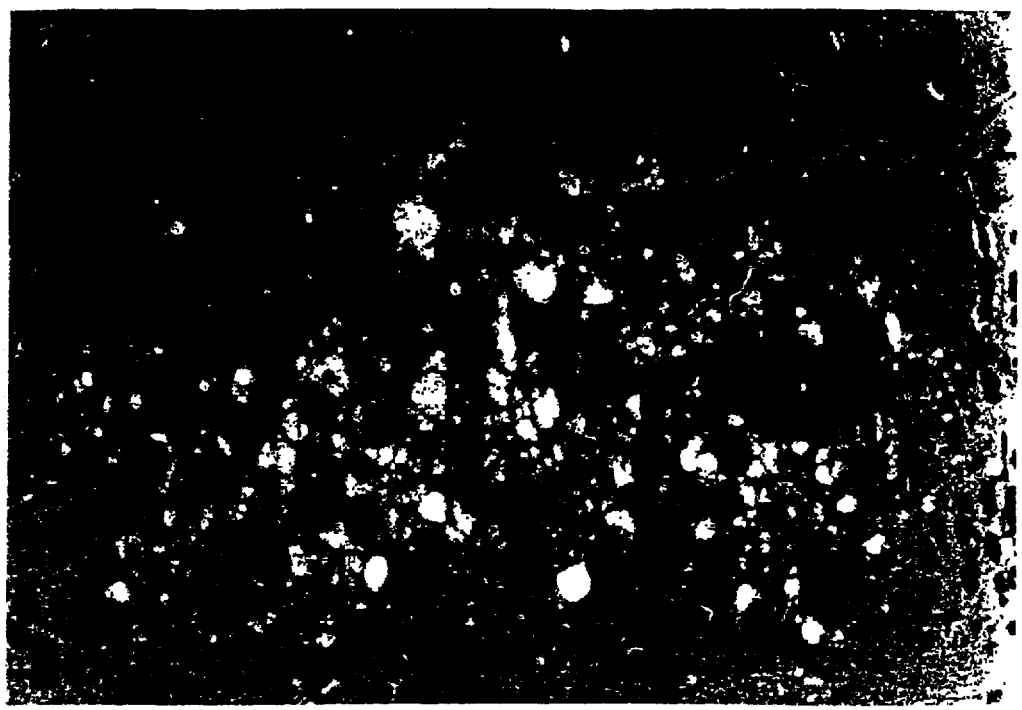
Figure 6D:
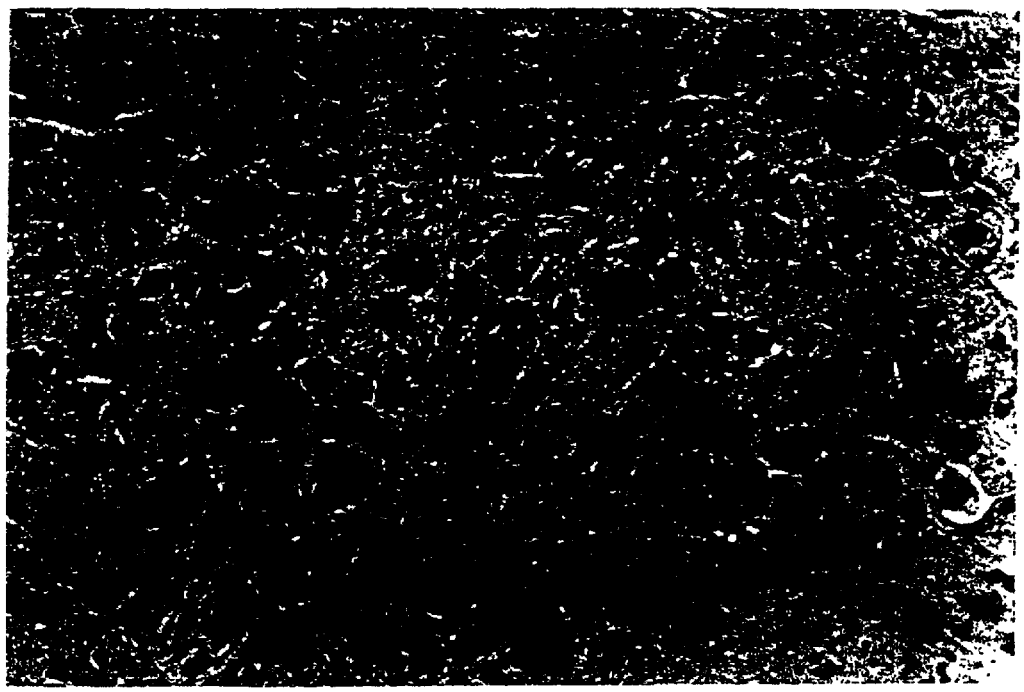
Figure 6E:
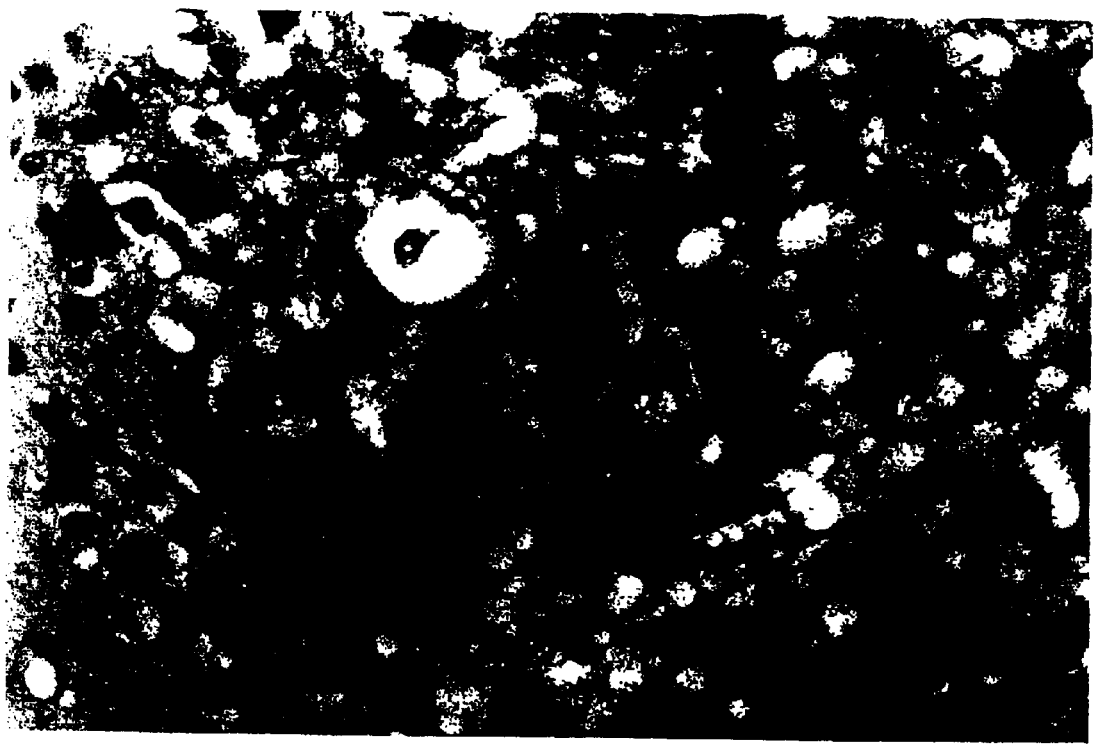

FIGS. 6A–6E are photographs of hematoxylin and eosin stained cortical and brainstem histology sections of treated Sod2CJE(−/−) and Sod2 (+/+) mice. FIG. 6A is a sagittal section of cortex from a 21 day old treated Sod2CJE(−/−) animal (50×); FIG. 6B is as in Panel A but a Sod2 (+/+) animal; FIG. 6C is a stained coronal section of the brainstem of a 15 day old treated Sod2CJE(−/−) animal, trigeminal motor nuclei (200×); FIG. 6D is as in 6C, but a Sod2 (+/+) animal; and FIG. 6E shows olivary nuclei of a 14 day old treated Sod2CJE(−/−) animal (400×).

Figure 7:
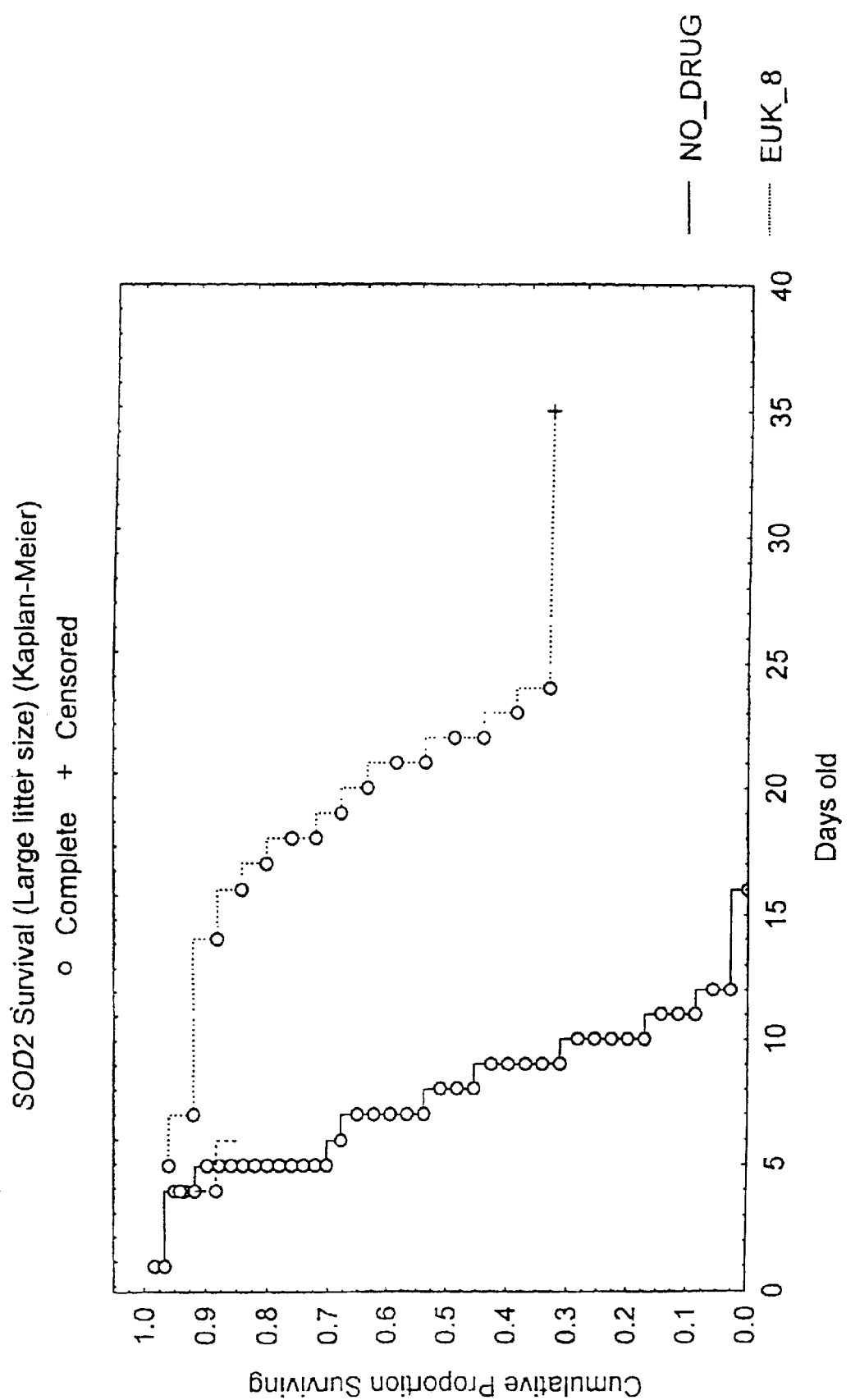

FIG. 7 graphically illustrates the effect of Euk-8 on lifespan of homozygous transgenic Sod2CJE(−/−) mice. The solid line represents lifespan of untreated controls; the dotted line represents lifespans of mice to which Euk-8 was administered at a dose of 30 mg/kg.

Figure 8A:
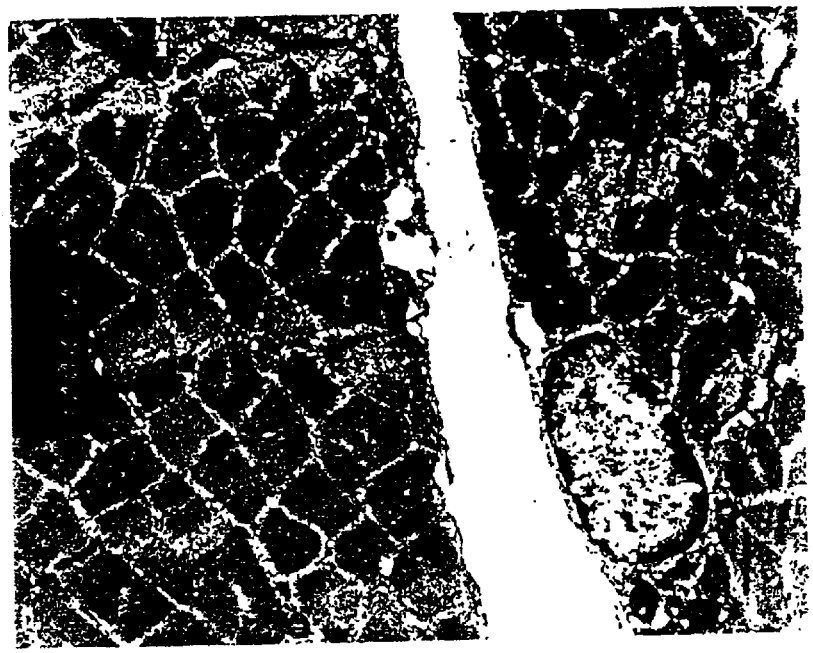
Figure 8B:

FIG. 8A is a photomicrograph of skeletal muscle tissue a 35-day-old wild type mouse. FIG. 8B is a photomicrograph of the skeletal muscle tissue of a 35 day old homozygous transgenic Sod2CJE(−/−) mouse; note the marked proliferation of mitochondria between the muscle fibers as well as beneath the sarcolemma.

DETAILED DESCRIPTION OF THE INVENTION

Oxygen radical-mediated tissue damage has been implicated in a variety of pathological conditions including, without limitation, ischemia reperfusion injury to brain and heart, Parkinson's disease, certain other neurodegenerative diseases, neonatal hyperoxic lung injury, atherosclerosis, mitochondrial disease, as well as normal aging. Thus, there is a need in the art for models systems and methods for testing potentially therapeutic compounds useful for the prevention, delay, or reduction of oxidative damage.

In the normal, healthy individual, most oxygen free radicals are produced by the mitochondria as byproducts of the electron transport processes of oxidative phosphorylation for physiological energy generation. Superoxide dismutase enzymes, glutathione peroxidase, and reduced glutathione function to protect the cells against the oxidative stress associated with normal cellular metabolism. Manganese superoxide dismutase (MnSOD) is located in the mitochondria and the expression of the nuclear gene encoding it is induced by a number of cytokines and by the superoxide free radical. Besides its role in protection against oxidative damage, MnSOD appears to function in differentiation and in tumor suppression.

The cytoplasmic SOD is a copper zinc enzyme (CuZnSOD). The gene encoding the cytoplasmic SOD is Sod1 [Weisiger and Fridovich (1973) *J. Biol. Chem.* 248, 4793–4796]. A genetic defect in Sod1 has been associated with familial amyotrophic lateral sclerosis (ALS), a disorder in which there is extensive motor neuron degeneration. A *Drosophila melanogaster* Sod1 mutant is viable, but it exhibits oxygen sensitivity, shortened lifetime, and female sterility. The Sod1 knockout mouse is viable, but it shows a somewhat increased sensitivity to stress [Reaume et al. (1996) *Nature Genetics* 13, 43–47]. Conversely, transgenic mice which overexpress the human Sod1 gene are less sensitive to cerebral ischemia damage than are normal mice.

A third mammalian SOD, also containing copper and zinc, is located largely extracellularly. Its gene is Sod3 [Carlsson et al. (1995) *Proc. Natl. Acad. Sci. USA* 92, 6264–6268]. Inactivation of this gene results in no overt phenotype.

MnSOD catalyzes the reaction $2O_2^- + 2H^+ \longrightarrow O_2 + H_2O_2$. Hydrogen peroxide is converted to oxygen and water by the action of catalase and/or glutathione peroxidase.

Li et al. (1995) *Nature Genetics* 11, 376–381 describes a mutant mouse in which the gene encoding mitochondrial MnSOD (Sod2) has been inactivated. The homozygote mutant genotype (MnSOD−/−) is lethal, with neonates dying by about 10 days of age. The heterozygous parents (MnSOD+/−) have no detectable abnormal phenotype through at least about 9 months of age, but MnSOD activity was about half that observed in the wild-type comparison mice (MnSOD+/+). No effect was observed on the CuZn-SOD activity levels in the homozygous (−/−) mice or the heterozygous mice (+/−).

As reported by Li et al. (1995) supra, the MnSOD (−/−) mice generally were dead by 10 days after birth, and at autopsy these animals had enlarged hearts, with myocardial hypertrophy, endocardial fibrosis, and a variety of degenerative changes. The clinical, pathological and biochemical data described by Li et al. (1995) supra suggested that the lack of functional mitochondrial SOD led to impaired mitochondrial functions in vital organs, especially the heart. Metabolic acidosis, ketosis, and accumulation of lipid in the liver and skeletal muscle reflect disruption of fatty acid metabolism as well. Thus, it was concluded that MnSOD functions to protect mitochondrial enzymes from oxidative damage by the superoxide radical anion produced as a byproduct of electron transport and oxidative phosphorylation. The MnSOD(−/−) mice also exhibited impaired cluster function of two iron-sulfur containing enzymes (succinic dehydrogenase, complex II, and aconitase, a tricarboxylic acid cyclic enzyme.

Presumably, superoxide anion levels rise in the mitochondria in the absence of functional MnSOD, and the superoxide anion is believed to react with the iron-sulfur clusters of various enzymes and enzyme complexes, several of which have been demonstrated to be superoxide-sensitive in vitro.

Oxidation of these enzymes impairs the function of the electron transport chain and the citric acid cycle, and accordingly, impairs energy generation and fatty acid oxidation.

The lack of the mitochondrial MnSOD in mice is characterized by death by 11 days of age in most animals (see, e.g., FIG. 3), dilated cardiomyopathy, metabolic acidosis, increased hepatic lipid levels, decreased aconitase activity and absence of cytochemically demonstrable respiratory chain complex II activity (succinic dehydrogenase). Most Sod2CJE(−/−) animals die between 3 and 13 days of age. A small proportion of untreated animals (12%) survive beyond 2 weeks of age, and the survival of Sod2CJE(−/−) animals as well as their rate of weight gain is noticeably increased in animals reared in small litter sizes of ≦6 pups (Table 1). Table 1 shows assessment of survival of Sod2CJE(−/−) animals reared in different litter sizes with and without MnTBAP administration. 6 Sod2CJE(−/−) animals were administered vehicle alone, and all died within one standard deviation of the mean life span of untreated animals in large litter sizes. Direct enzyme assay of MnSOD in heart mitochondria reveals that complex II activity is decreased by 72% relative to wild-type mouse heart mitochondria (p=0.002), complex I (NADH dehydrogenase) by 45% (p=0.03), and citrate synthase activity by 33% (p=0.03).

Figure 1:
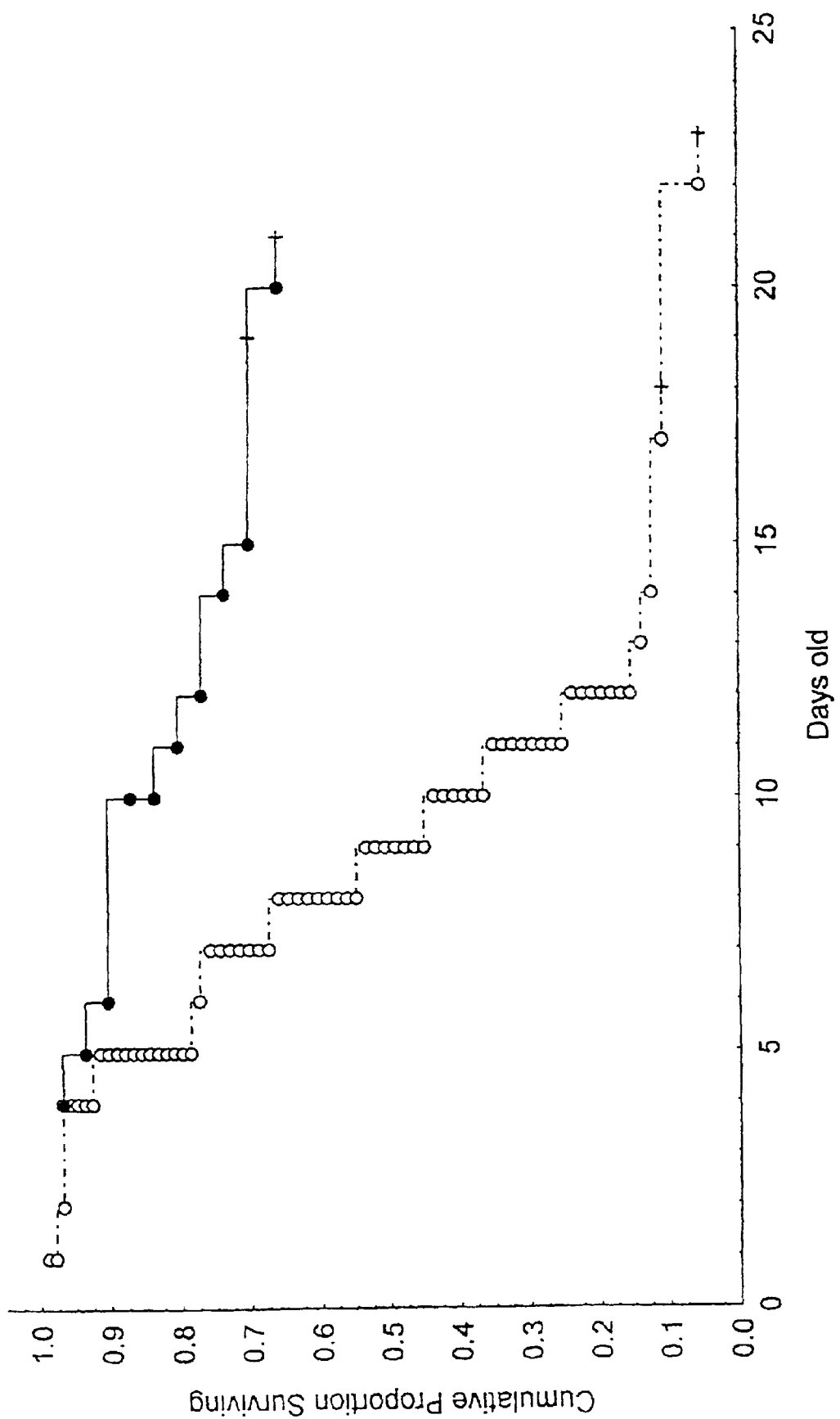
FIG. 1 illustrates Kaplan and Meier survivorship analysis of Sod2CJE(−/−) animals. Sod2CJE(−/−) animals reared in all litter sizes; with (•)(n=31) and without (o) (n=94) MnT-BAP administration. (o)—complete observations, (+)—censored observations. This graph includes data from experiments in which the litter size was restricted to six or fewer pups pooled with data from experiments in which the litter size was not restricted. The sizes of unrestricted litters were typically about 12 pups. A dramatic increase in survival (to about three weeks of age) is manifest upon treatment with MnTBAP in the Sod2CJE(−/−) animals.
Figure 2:
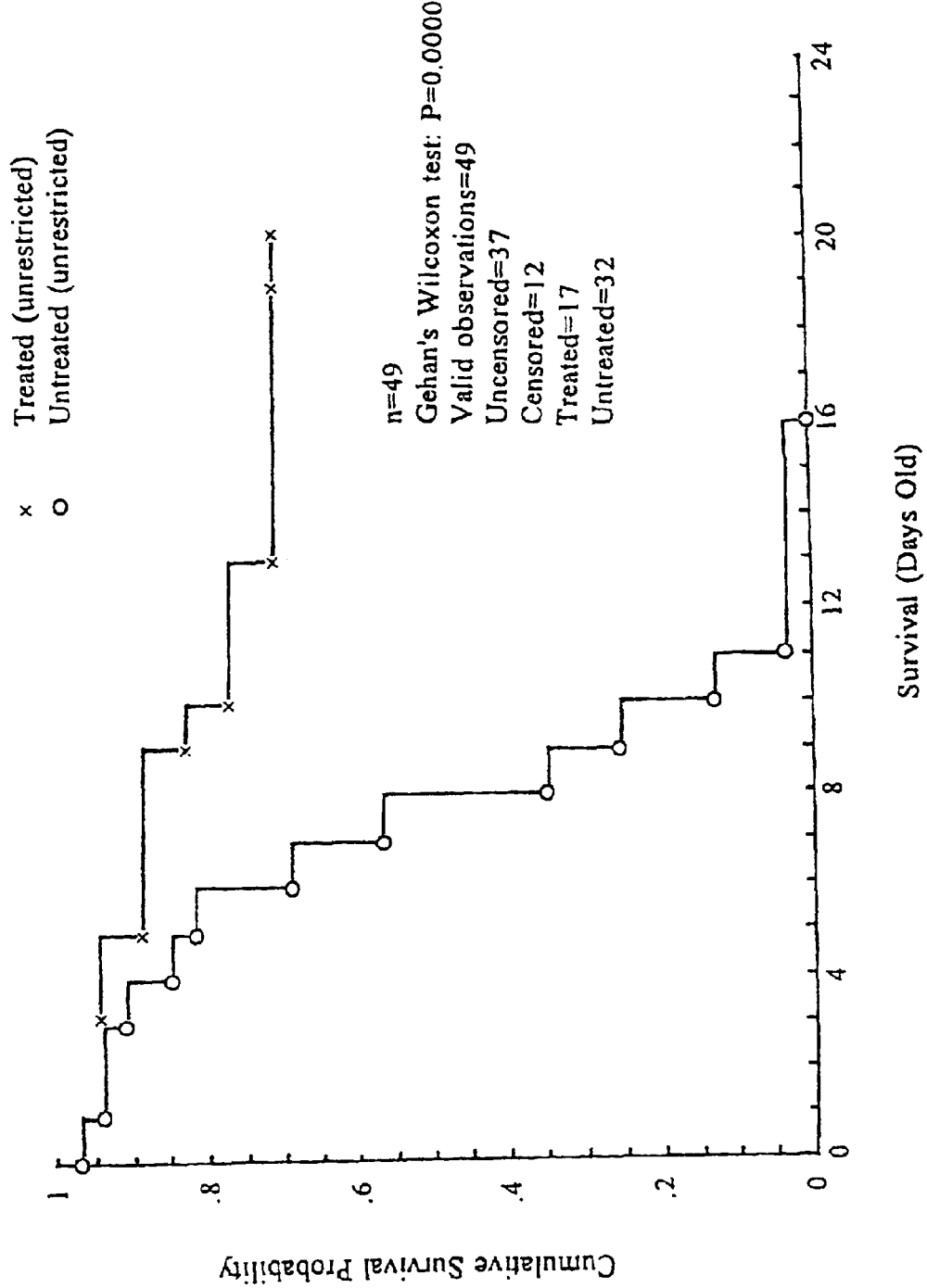
FIG. 2 provides a graphical display of the cumulative survival probability over time for Sod2CJE(−/−) mice (mice as described in Li et al. (1995) Nature Genetics 11:376–381)

The antioxidant and MnSOD mimetic Manganese 5,10, 15,20-tetrakis(4-benzoic acid) porphyrin (MnTBAP) was administered in an attempt to ameliorate the Sod2CJE(−/−) phenotype. MnTBAP is known to catalytically degrade superoxide anion in vitro, being equivalent to about 10% the activity of Sod1/Sod2 when compared by weight [Day et al. (1995) *J. Pharmacol. Exp. Ther.* 275, 1227–1232]. In vitro [Day et al. (1995) supra] and in vivo [Day and Crapo (1996) *Toxicol. Appl. Pharmacol.* 140, 94–100] studies indicate that MnTBAP is permeable to cells but does not cross the blood-brain barrier in mice after that barrier is established at about 7–12 days of age. MnTBAP has also been shown to protect mammalian cells from paraquat-induced injury in vitro, to protect neuronal aconitase after challenge with paraquat and to prevent excitotoxic cell death in neuronal cell cultures exposed to glutamate agonists. Untreated Sod2CJE(−/−) mice die at 8.3±4.4 (SD) days of age (range 1–23, n=94). By contrast, 70% of the MnSOD(−/−) mice treated with 5 mg/kg MnTBAP daily by intraperitoneal injection lived to greater than or equal to 20 days of age (n=31) with a mean age of survival of 16.4±5.8 days. FIG. 1 shows the survival curves. This differential survival was also mildly affected by litter size. For litters of more than six pups (unrestricted) the mean age of survival without MnTBAP was 6.5±2.9 versus 16.1±6.6 days with MnTBAP (FIG. 2) and for litters with six or less pups (restricted) the mean survival with MnTBAP was 11.4±4.8 versus 16.6±4.9 days without MnTBAP (FIG. 3).

Despite the increased survival, the present inventors were surprised to note that the treated mice exhibited progressive motor impairment with bradykinesia, limb paresis, repetitive movements and limb dystonia. Animals surviving to 20–22 days had normal hepatic lipid and no cardiopathy. Neuropathological analysis revealed prominent spongiform changes in multiple cortical and subcortical regions and several brain stem motor control nuclei. The failure of MnTBAP to prevent brain damage in the MnSOD knockout mice reflects the failure of this compound to cross the blood-brain barrier, which closes in mice after about 7–12 days of age. The ability of MnTBAP to modulate the effects of endogenously produced reactive oxygen species in vivo through the use of a mouse model deficient in the production of mitochondrial SOD allows the rapid assessment of drugs potentially able to ameliorate diseases that have free radical effects implicated in their pathogenesis. The increase in longevity and improved physical parameters were not due to the MnTBAP solvent (vehicle) (Table 1).

The dilated cardiomyopathy characteristic of untreated Sod2CJE(−/−) animals is apparent at 6 days of age (FIG. 5A compared to FIG. 5B) [Li et al. (1995) supra]. MnTBAP treatment prevented the cardiac defect in the Sod2CJE(−/−) animals (FIG. 5C). In controls (+/+, +/−), no significant difference was observed between the hearts of animals treated with MnTBAP and untreated animals. Moreover, control animals treated with MnTBAP exhibited no pathological changes in liver or brain, indicating that MnTBAP was not toxic.

Untreated Sod2CJE(−/−) mice accumulate a massive amount of lipid in the liver which can be demonstrated by Oil red-O staining [Li et al. (1995) supra] (see also Table 2). Table 2 shows the results of qualitative assessment of lipid in liver by Oil red-O staining in treated Sod2CJE(−/−) and (+/+) animals of varying ages. The level of lipid in liver sections was scored as follows: 0=no observable lipid in sections, 1=mild diffuse speckled distribution of lipid, 2=more intense speckled pattern, 3=coalescence of small lipid droplets into large intercellular droplets, and 4=massive intercellular lipid droplet accumulation. Wild-type or heterozygotes treated with MnTBAP for 3 weeks had no observable difference in the morphology of the liver compared to untreated controls (+/+or +/−). The livers of 25 MnTBAP treated Sod2CJE(−/−) animals were examined at 12, 14 and 17 days of age (Table 2) and compared with treated wild type animals. Of the MnTBAP treated Sod2CJE (−/−) animals, only 8% (2/25) had lipid levels comparable to those seen in untreated Sod2CJE(−/−) animals of 6–10 days of age. The remainder of the treated Sod2CJE(−/−) animals had lipid levels comparable to treated controls. Hence, MnTBAP markedly reduced the lipid levels in the mutant mice.

The MnTBAP treated Sod2CJE(−/−) animals, which are rescued from early neonatal lethality, survive to develop a striking movement disorder, characterized by gait abnormality and tremor. The gait disturbance began at about 12 days of age, characterized by poor coordination of hindlimb movements with ambulation (ataxia), alternating extensor dystonic-like posturing of hindlimbs, and pivoting on the extended limb. Over the ensuing days, hindlimb ataxia worsened and spread to involve the forelimbs, accompanied by intermittent head tremor. By the mid and later stages, the affected animals exhibited a wide based gait, swaying from side to side, followed by frequent falls to either side, sometimes resulting in multiple rolls (barrel rolls). Animals had difficulty righting and attempts were accompanied by a mild, intermittent tremor of the limbs. By 21 days of age, most of the Sod2CJE(−/−) animals were essentially moribund and immobile, and were declining in weight rapidly, and were therefore euthanized. There are some behavioral similarities to the recently reported Sod2m1BCM [Lebovitz et al. (1996) *Proc. Natl. Acad. Sci. USA* 93, 9782–9787] mice with circling, and the progressive motor and behavioral abnormalities.

Histological analysis of the brains of MnTBAP-treated and untreated Sod2CJE(−/−) animals which survived to greater than 14 days of age revealed prominent spongiform changes (vacuolization of brain parenchyma). These spongiform changes were typically observed in large regions of the cortex (FIG. 6A) and focally within nuclei of the brainstem (6C, 6E). Vacuoles were observed within the neuropil and occasionally within neurons (FIG. 6E). Vacuoles compressed intraneuronal and extraneuronal structures, nissl substance, and nuclei. Fine membranous strands, which may reflect the coalescence of multiple small vacuoles, were often observed within the larger vacuoles.

Vacuolization of cortical gray matter was seen in 14 out of 14 Sod2CJE(−/−) (10 treated, 4 untreated) mice examined at 14–22 days of age. This must develop rapidly, since an 11-day-old non-treated Sod2CJE(−/−) mouse did not demonstrate any neuropathology, and untreated Sod2CJE(−/−) mice do not manifest any neuropathology up till 10 days of age [Li et al. (1995) supra]. The cortical spongiform changes were moderate to severe in 9 of 14 cases and involved primarily the mid to lower cortical layers and immediate subcortical white matter. Frontal cortical regions were most significantly and consistently affected. Mild changes were also observed in other cortical regions including the subiculum, parietal, temporal, and entorhinal cortex. Of 3 treated animals examined between 14 and 15 days of age, mild spongiform changes were observed in cortical gray matter. There was no apparent relationship between the severity of cortical changes and age.

Variable degrees of vacuolization were also seen in selective regions of the brainstem and cerebellum in 7 of 14 cases. Certain brainstem regions shared particular vulnerability. Brainstem vacuolization was most commonly observed in the reticulotegmental nucleus of the pons, the superior, and medioventral periolivary nuclei, and in the regions of the motor nucleus of cranial nerves V and VII. In some cases, vacuoles were also observed in the region of the lateral superior olive, and the reticular nuclei of the pons and the medulla. The striatum, substantia nigra, cerebellar cortex, and hypoglossal nuclei showed no major changes. In 2 of 3 treated mice examined at 14 and 15 days of age, brainstem vacuolization was prominent and comparatively more severe than the cortical spongiform changes described above (FIGS. 4C, 4E).

Mitochondrial DNA (MtDNA) from cortex of 21 day old MnTBAP treated Sod2CJE(−/−) animals (n=2) was examined for mitochondrial DNA rearrangements by long extension PCR and field inversion electrophoresis of unrestricted mtDNA [Melov et al. (1997) Nucleic Acids Res. 25, 974–982]. No significant differences were found relative to treated controls (n=2).

Although the molecular pathogenesis of the pronounced spongiform encephalopathy is unclear at present, a clear similarity exists in histopathology between a recent mouse model of ALS [Wong et al. (1995) Neuron 14, 1105–1116] and the neuropathology of the MnTBAP treated Sod2CJE (−/−) mice. The G37R mutation of Sod1 associated with familial ALS, when overexpressed in 4 out of 4 lines of transgenic mice, results in pronounced vacuolar degeneration of the mitochondria [Wong et al. (1995) supra]. The G37R mutation also caused vacuolar changes observable under light microscopy in the brainstem motor neurons of cranial nuclei V and VII. Hence, there are commonalties between regional localization of spongiform changes in the Sod1G37R mouse and the MnTBAP-treated Sod2CJE(−/−) mouse.

Since MnTBAP diffuses through all viscera, and does not cross the blood brain barrier, it follows that the neurodegenerative disease which afflicts the MnTBAP treated Sod2CJE(−/−) animals is the product of damage to the brain caused by the excessive production of reactive oxygen species (ROS) by the mitochondria. This is consistent with other reports suggesting that ROS, mitochondrial defects and associated ROS generation, play an important role in a variety of neurodegenerative diseases including dystonia, ALS, Parkinson's Disease, Alzheimer Disease, and aging [Yim et al. (1996) Proc. Natl. Acad. Sci. USA 93, 5709–5714; Wallace, D. C. (1996) "Mitochondrial DNA Mutations and Bioenergetic Defects in Aging and Degenerative Diseases," in Molecular and Genetic Basis of Neurologic Disease (eds. Rosenburg, D. N. et al.) pp. 237–269, Butterworth Heinemann, Boston, Mass.; Szabo, C. (1996) "Physiological and Pathophysiological Roles of Nitric Oxide in the Central Nervous System," Brain Research Bulletin 41, 131–141; Simonian and Coyle (1996) Annu. Rev. Pharmacol. Toxicol. 36, 83–106; Beal, M. F. (1995) Ann. Neurol. 38, 357–366; Halliwell, B. (1992) J. Neurochem. 59, 1609–1623; Hensley et al. (1995) Proc. West Pharmacol. Soc. 38:113–20; Mattson, M. P. (1994) Ann. NY Acad. Sci. 747, 50–76]. MnTBAP-treated and/or Euk-8 Sod2CJE(−/−) animals provide an excellent model system for screening for new drugs to treat neurodegenerative diseases and for the testing of hypotheses related to free radical-mediated aging.

Prior to the present invention, it could not have been known that neurological damage could be a result of the mitochondrial MnSOD deficiency because the neonate mice did not survive long enough to develop overt symptoms of neuropathy. It was surprising that there were lesions in the brains of the mice treated with MnTBAP and that there were behavioral reflections of central nervous system damage.

Subsequent to our recognition of neurological disorders in the homozygous Sod2CJE (−/−) mice described by Li et al. (1995) supra, which were treated with MnTBAP, we learned of a second MnSOD-deficient mouse which is described by Lebovitz et al. (1996) Proc. Natl. Acad. Sci. USA, 93, 9782–9787. In this mouse the first two exons of Sod2 are deleted. As in the mouse described by Li et al. (1995) supra, the mutation is propagated in heterozygotes, with homozygous animals identified among the progeny of the heterozygote×heterozygote mating. These Sod2m1BCM (−/−) mice are reported to survive up to about 18 days, and they exhibit symptoms including anemia, ultrastructural evidence of neuron degeneration in the basal ganglia and brainstem, and motor abnormalities including weakness, rapid fatigue and circling behavior. About 10% of the Sod2m1BCM(−/−) mice exhibit enlarged and dilated hearts [Lebovitz et al. (1996) supra].

Euk-8 (Eukarion, Bedford, Mass.) [see U.S. Pat. No. 5,403,834 to Malfroy-Camine and Baudry, issued Apr. 4, 1995; Doctrow et al. (1997) Adv. Pharmacol. 38, 247–268] is a known scavenger of free radicals such as superoxide and a known antioxidant. Other salen-metal complexes which function as antioxidants and/or free radical scavengers can also be used in the animal model of the present invention to prolong the lifespan of the Sod2CJE homozygous mouse so that neurobehavioral and other physiological symptoms resulting from MnSOD deficiency can be observed and in which the prevention or delay of such symptoms can be monitored after the administration of a test compound.

Euk-8 is even more effective at prolonging the life of Sod2CJE(−/−) mouse pups than MnTBAP (See FIG. 7). Mice which received Euk-8 on a daily basis at a dose of 30 mg/kg have a mean life-span of 22 days as opposed to a mean life-span of 16 days for MnTBAP-treated pups and a mean life-span of 7 days for untreated MnSOD-deficient mouse pups (See also Table 4). Euk-8 has been shown to be effective in an MPTP model of Parkinson's disease. N-methyl-4-phenyl-1,2,3,6-tetrahydropyridine (MPTP) is a neurotoxic compound which selectively inhibits Complex I in the respiratory chain. When administered to rodents and primates, it causes degeneration of the substantia nigra, thereby providing a chemical lesion model of Parkinson's disease [Schapira et al. (1993) *Biochem. Soc. Trans.* 21, 367–370]. Euk-8 is also known to ameliorate β amyloid protein toxicity in neuronal cell culture and to be protective in ischemia/reperfusion models.

The most striking finding from the use of Euk-8 in the Sod2CJE(−/−) mouse is the rescue of the neurological and behavioral phenotype seen the MnTBAP-treated mouse manifesting between 14 and 16 days of age. Euk-8 shows beneficial effects on neuronal function, indicating that the compound affects the central nervous system and that it crosses the blood brain barrier. The increased neurological effectiveness of Euk-8 in comparison to MnTBAP indicates that it is possible to screen different compounds rapidly and easily for effectiveness in preventing free-radical mediated disorders of the central nervous system in the particular MnSOD(−/−) mouse exemplified herein.

Although the Euk-8 treated animals exhibit significantly less neurological toxicity than isogenic animals treated with MnTBAP, the Euk-8 treated animals do eventually develop neurobehavioral disorders. The spongiform encephalopathy seen at 17 days in the MnTBAP-treated mouse is absent; therefore, the Euk-8 is selectively targeted to different regions of the brain. Moreover, the Euk-8 treatment uncovers a new neurological phenotype, i.e., auditory induced seizures. Although the Euk-8 treated animals are essentially normal at 21 days, soon thereafter they develop a marked sensitivity to sound. This is manifested by sound-induced hyperkinetic seizures. These seizures are characterized by a period of intense hyperkinetic behavior in response to a simple repetitive audio stimulus (for example, snapping of the fingers), shortly followed by a completely debilitating seizure characterized by complete rigidity and hyperextension of all limbs along the longitudinal axis of the body for about 10–20 seconds. During this period, the mouse is so rigid that it can be picked up by any region, and it maintains the extended posture despite its orientation. These seizures can be induced sequentially shortly after the animal has returned to normal behavior. Not all Euk-8 animals which survive to 21 days develop the seizures (5 of 9 tested thus far). This propensity for seizure persists to about 4 weeks of age and thereafter, auditory induced seizures no longer can be elicited. After about 4 weeks of age, the animals begin to develop a similar behavioral phenotype to that observed in the MnTBAP-treated animals of about 15 days of age. The neurobehavioral disorder worsens over the course of the following week, and the animals are sacrificed at 5 weeks of age.

The behavioral phenotype (hyperkinetic behavior, tremor and rigidity) is consistent with the outward effects of Parkinson's disease in humans. The incomplete efficacy of the Euk-8 in the present MnSOD-deficient mouse allows the use of the Euk-8 treated animals in the identification of antioxidant compounds which are targeted to and protective of this region of the mammalian brain. Thus, prevention of the neurobehavioral disorders at about 3–5 weeks of age in the MnSOD-deficient homozygous mouse which has been treated with Euk-8 allows the identification of compounds with therapeutic potential for the prevention of Parkinsonism. This emphasizes the usefulness of the MnSOD(−/−) mouse model for investigation of antioxidants with effectiveness in different portions of the brain.

In addition to the phenotype related to the central nervous system of the Euk-8 treated mouse, the skeletal muscle of those mice also exhibits cytopathology. Ultrastructural examination of skeletal muscle of Euk-8 treated mice at 5 weeks of age (n=5) shows that there is marked proliferation of mitochondria in between muscle fibers as well as beneath the sarcolemma in comparison to treated wild-types of the same age (see FIG. 9). These changes are characteristic of mitochondrial myopathy and Euk-8 treated mice provide the first demonstration that a defect in mitochondrial fee-radical defenses causes mitochondrial myopathy. Like the neurological phenotype, the skeletal muscle myopathy is not observed in untreated MnSOD-deficient homozygotes which die at an early age (before about 10 days of age) [Li et al. (1995) supra]. Thus, animals which have been treated with an antioxidant such as MnTBAP or Euk-8 can be used for the screening of antioxidants which will prevent or delay the onset of the mitochondrial myopathy phenotype in skeletal muscle.

Besides the mitochondrial myopathy, there is also evident focal degeneration of myofibers. Another striking feature is the apoptotic nuclear morphology of myonuclei (See FIG. 9B). These morphological hallmarks can be used as markers to develop compounds which prevent these phenotypes in MnSOD-deficient homozygous mice where those compounds are useful to prevent muscle wasting diseases in which free radicals contribute to the disease etiology.

In the untreated MnSOD-deficient homozygotes, the presence of the oxidative phosphorylation enzyme succinate dehydrogenase (SDH, Complex II), which can be demonstrated by histochemical staining in skeletal muscle, is greatly reduced, indicating a loss of activity. Fat accumulates in the liver, where it can be detected by Oil Red O staining. In the MnTBAP-treated mice, the accumulation of lipid in the liver is reduced but tissue SDH is still inhibited. By contrast, in Euk-8 treated animals both the lipid accumulation in the liver and SDH inhibition are rescued. Hence, Euk-8 is more effective than MnTBAP in rescuing metabolic defects as well as in delaying neurobehavioral disorders resulting from free radical damage in the central nervous system.

The Sod2CJE(−/−) mice provide a model system in which to test potentially therapeutic compositions, particularly antioxidant, free radical scavengers and/or SOD mimetic compositions, for the ability to prevent fatal damage from endogenous oxygen free radicals, especially those generated in the mitochondria. Those SOD mimetics which do not cross the blood-brain barrier protect the MnSOD(−/−) mice from death due to cardiomyopathy at an average of 7 days after birth as seen in the untreated control homozygous Sod2CJE(−/−) mice. In MnTBAP-treated mice, cumulative free radical damage to the central nervous system (CNS) results in an inability to feed and move, and hence total debilitation by about three weeks of age. In the Sod2m1BCM mice described in Lebovitz et al (1996) supra, the Sod2m1BCM mice show less severely impaired body and cardiac function as compared to the Li et al. (1995) supra untreated mice, but oxidative damage to the CNS ultimately causes death at 2–3 weeks of age. Thus, those compounds having the ability to cross the blood-brain barrier are identified using the present methods and the Li et al. (1995) supra mice and/or the Lebovitz et al. (1996) supra mice. In the Li et al. (1995) supra Sod2CJE(−/−) mice, those compounds prolong survival past about three weeks of age and postpone the onset of overt symptoms of neurological damage past the 2–3 week age where such damage became apparent in those mice treated with MnTBAP, which does not cross the blood-brain barrier to a significant extent. Comparable assessment of drugs which cross the blood-brain barrier is also possible in the mice described by Lebovitz et al. (1996) supra. Thus, in Sod2CJE(−/−) mice, therapeutic antioxidant (and/or free radical scavenging) compositions having protective effects against oxygen free radicals and which do cross the blood-brain barrier are identified using the present methods as those which prolong survival significantly past about three weeks and which prevent or postpone the onset of obvious oxidative damage to the CNS significantly past about two to three weeks of age.

In addition to the histological and behavioral abnormalities in the central nervous system and certain other tissues of the homozygous MnSOD mutant mice which were treated with an antioxidant so as to prolong survival, the present inventors determined that there was evidence of apoptosis in affected tissues in those Sod2CJE(−/−) mice. Apoptosis is the programmed cell death and destruction of cells in response to certain intrinsic or extrinsic stimuli. Reactive oxygen species are known inducers of the apoptotic pathway.

Because the spongiform changes in the brain tissue of the MnTBAP-treated mice could be associated with apoptosis, the levels of mRNAs associated with the induction of apoptosis were measured in the MnTBAP-treated mouse brain. By carrying out RNase protection assays for 13 genes involved in apoptosis, it was determined that 4 of these were differentially regulated in the brainstem between wild-type and MnTBAP-treated Sod2CJE(−/−) mice at 12 days of age but not at 14 or 17 days of age (Table 3). The expression of all 4 of these genes was up-regulated by between 13 and 25% in the MnTBAP-treated Sod2CJE(−/−) animals relative to the wild-type mice; this difference is highly statistically significant. Thus, without wishing to be bound by theory, it is concluded that the abnormalities in specific regions of the brains of homozygous MnSOD-deficient mice are due at least in part to apoptosis.

The FLICE (Fas associated death domain Like ICE (interleukin-1β-converting enzyme) shows homology to the ICE-like proteases responsible for degrading the cell once the apoptotic program has been initiated. These proteases have unique targets within the cell; many of those targets are unknown. FLICE is part of the family of proteases which belong to the "Yama" family of proteases, so-called due to their similarities to the Yama/CPP32/apopain protease. This family is believed to execute the death signal of the cell. The highly significant increase in this pre-apoptotic message between the treated wild-type and treated Sod2CJE(−/−) animals shows that the apoptotic pathway is initiated within the brainstem of the homozygous Sod2CJE-deficient animals at 12 days of age. However, there was no difference in 14 and 17-day-old mice, presumably due to the apoptotic execution being essentially complete by 12 days of age. This is consistent with the remarkable rapidity with which the neurodegenerative phenotype appears and with which apoptosis is carried out.

The identification of apoptosis, in association with increased mitochondrial generation of free radicals within the central nervous system, has implications including the following: MnTBAP-treated MnSOD-deficient homozygotes can be used to identify genes which are involved in apoptosis within the central nervous system, and this animal model can be used to screen antioxidants for their efficacies as anti-apoptotic compounds in the brain and other organs.

In addition to the pro-apoptotic induction of FLICE, the inventors also documented the transcriptional induction of anti-apoptotic genes including the following: Bfl-1, Bcl-W and Bcl-X. It is postulated that the cell is attempting to compensate for inappropriate levels of free radicals and so induces anti-apoptotic defenses in an attempt to prevent apoptosis. However, in view of the neuropathological evidence of widespread spongiform encephalopathy, this is clearly ineffective. Hence, this animal model can be used to identify anti-apoptotic genes, and such genes are useful as therapeutic targets for diseases in which apoptosis is implicated.

All references and patent publications cited in the present application are incorporated by reference herein.

The following examples are provided for illustrative purposes, and are not intended to limit the scope of the invention as claimed herein. Any variations in the exemplified methods which occur to the skilled artisan are intended to fall within the scope of the present invention.

EXAMPLES

Example 1

Animal Model

Mice lacking functional MnSOD have been described by Li et al. (1995) Nature Genetics 11:376–381, incorporated herein by reference. The genotypes of one-day-old pups are determined by genetic analysis of tissue surgically excised from the toe or tail tip (2–3 mm). In these mice the third exon of the Sod2 gene has been deleted, thus, destroying the ability to synthesize an active mitochondrial MnSOD.

Genetic analysis of tissue in 2 day old mouse pups is done by first extracting DNA from each tissue sample using Proteinase K digestion (30 min) and then carrying multiplex polymerase chain reaction using three primers, one shared (A, 5'-CGAGGGGCATCTAGTGGAGAAG-3'; SEQ ID NO:1) and one each per mutant (C, 5'-CACACATCGGGAAAATGGTTT-3'; SEQ ID NO:2) and for normal (B, 5'-TTAGGGCTAGG-TTTGTCCAGAA-3'; SEQ ID NO:3) alleles. Tail tips were lysed, vortexed, and used in a biphasic PCR reaction using PCR Gems 50 (trademark of Perkin Elmer, Foster City, Calif.) (0.4 μM primers, 200 μM dNTPs, 1 unit Taq (Gibco/BRL, Gaithersburg, Md.), 1× PCR buffer (67 mM Tris-HCl pH 8.8, 16 mM $(NH_4)_2SO_4$, 10 mM mercaptoethanol, 2 mM $MgCl_2$, 10% Dimethyl sulfoxide, DMSO). Reaction conditions were as follows: hot start followed by 30 cycles of 98° C., 30 sec; 58° C., 30 sec; 72° C., 30 sec. Alternatively (volume of 25 μliters) contains DNA (20 to 100 ng), 20 mM Tris, pH 8.9, 10 mM KCl, 10 mM $(NH_4)_2SO_4$, 200 μM nucleotides, primers, 2 mM $MgSO_4$, 0.1% Triton S-100, 0.1 mg/ml nuclease free bovine serum albumin, and 0.02 units/μliter Taq DNA polymerase. Amplification products were then analyzed by agarose gel electrophoresis using 1.2% agarose gels. Genotype/PCR analysis results in the production of an amplimer of about 500 bases for the wild-type gene and an amplimer of about 350 bases for the mutant gene (as described in Li et al. (1995) supra). The homozygous MnSOD (−/−) mouse DNA produces only the 350 base amplification product, the wild-type mouse DNA produces only the 500 base product, while the heterozygote produces amplimers of both sizes due to the presence of both forms of the gene. The skilled artisan understands that alternative primers can be used and amplification products can be expected for these mice or where a different disruption of the Sod2 gene is used. Absence of the MnSOD activity can be confirmed by enzymatic assay carried out as described in Marklund, S. L. (1985) in Direct Assay with Potassium Superoxide, ed. R. A. Greenwald, CRC Press, Boca Raton, Fla., pp. 245–255 or as described by Li et al. (1995) supra.

Example 2

Animal Husbandry

Mice are housed under standard animal housing conditions with a normal day/night cycle and fed normal mouse chow (not high-fat) (Labdiet 5001, PMI Feeds Inc., St. Louis, Mo.). Nursing mothers are housed in individual cages with their offspring. They have free access to food and water (ad libitum. Fresh bedding and a change of cage litter are provided twice per week.

Litters were grouped into two sizes: large, >6 pups/litter of mutant, heterozygous and normal pups; and small, ≦6 Sod2CJE(−/−) pups/litter, in which the wild type and heterozygous pups were removed at three days of age to ensure that the homozygous mutant pups had unrestricted access to food and nurturing.

Test mice are weighed daily to allow calculation of appropriate dosage, but otherwise, handling is kept to a minimum to reduce stress on the nursing mother.

Example 3

Preparation of MnTBAP

H$_2$TBAP (5,10,15,20-tetrakis [4 benzoic acid]) porphyrin (Aldrich, Milwaukee, Wis.) at 85% purity was used as the starting material. H$_2$TBAP was dissolved in dimethyl formamide (DMF) and refluxed overnight at 80° C. in the presence of excess manganese chloride while bubbled with room air. The reaction product was chilled in an ice bath upon which the product precipitated out of solution. The filtrate was washed several times with ice cold water and dried in a vacuum oven. The resultant product, termed MnTBAP in this report, was found to be >91% pure by HPLC analysis using a Microsorb MV C18 column. Elemental analysis on MnTBAP-DMF was performed and the results were as follows, calculated for $C_{48}H_{27}N_4O_8$—$H_2O$—$C_3H_7NO$: C, 65.60; H, 3.89; N, 7.5; Mn, 5.88; found: C, 65.62; H, 3.7; N, 7.13; Mn, 4.66.

In most experiments, MnTBAP was prepared for injection by dissolving in 0.1 M NaOH, diluted with sterile water to a dosage level of 5 mg MnTBAP/kg, and administered by daily intra-peritoneal (IP) injections of between 10 and 45 µl, 2 hours post weighing, from 3 days of age. In addition to homozygous mutant animals, both heterozygotes and wild-type animals were injected to serve as controls. Wild-type or heterozygous Sod2CJE pups were sacrificed at the same age as Sod2CJE(−/−) pups to serve as controls.

Example 4

Administration of Test Compounds

Mouse pups are injected intraperitoneally with test compounds with a 50 microliter Hamilton syringe and a 31 G needle. The maximum volume administered to pups younger than 6 days of age is 20 µl. Injections are given daily, at the same time per day ±2 hours.

The MnTBAP stock solution is diluted down to the administered dose, which is dependent on body weight. For MnTBAP, the dosage is 5 mg/kg per day. Pups are weighed daily to allow calculation of the appropriate dosage.

Other compounds are prepared in a similar manner, with care taken not to administer a toxic dose.

Example 5

Statistical Analysis

Survival analysis was carried out by examining the animals daily to determine mortality, and entering the results into a life-table in the program Statistica (Statsoft, Tulsa, Okla.). Comparison between groups was carried out using the Kaplan and Meier survival function, non-parametric t-tests, and the Gehans Wilcoxon statistic from within the program to compare groups.

Example 6

Behavioral Analysis

Treated Sod2CJE(−/−) animals were observed daily from 10 days through to greater than five weeks for behavioral abnormalities compared to litter mate controls. Daily video recordings of up to 10 minutes were made to longitudinally track the development of behavioral changes. A total of 187 video recordings were made of 63 animals from 10 to 23 days of age.

Example 7

Neuropathology, Cardiac Measurements, and Histology

For pathology, the brains were removed from the sacrificed animals and fixed in 10% buffered formalin for up to 7 days. They were then processed, embedded, and sectioned. In some cases representative sections were made every 20 sections or so at 7 microns thickness throughout the brain and stained with hematoxylin and eosin for examination by light microscopy. In other cases, the entire brain was sectioned at 8 microns throughout. Fifteen Sod2CJE(−/−) brains between 11 and 23 days of age were examined by hematoxylin and eosin staining and light microscopy in coronal, sagittal, or horizontal orientations with 17 controls in a blinded study (4 heterozygotes and 6 wild-types treated; and 2 heterozygotes and 5 wild-types untreated).

Cardiac dimensions were measured at 21 days of age for wild-type and heterozygous animals. These were compared with homozygous mutant animals treated with MnTBAP as described [Li et al. (1995) supra].

Assessment of the effect of MnTBAP treatment on liver morphology was carried out by blind assessment of wild-type and heterozygous animals chronically treated with compound for 3 weeks. Hematoxylin and Eosin stained sections from 27 treated homozygous normal (+/+) and heterozygous (+/−) animals were compared with 2 untreated control animals. To evaluate lipid in the liver of treated homozygous mutant MnSOD(−/−) animals, 8 u frozen sections were prepared and stained with Oil red O [Li et al. (1995) supra]. Each section was evaluated for the quantity and size of lipid droplets by arbitrarily scoring with a numerical value (Table 2). The ratings of multiple animals were then averaged.

Example 8

Evaluation of Test Compounds

After 20 days of age, the MnTBAP-treated Sod2CJE(−/−) pups are generally severely affected by the neurological phenotype. They are sacrificed and brain, heart, kidney, lung, hind-limb skeletal muscle and liver tissues are harvested and either frozen for MnTBAP analysis or frozen with dry ice or in liquid nitrogen-cooled isopentane or fixed with formaldehyde or glutaraldehyde for pathology and histological evaluation. Where desired, organ or tissue samples are frozen for subsequent DNA extraction and analysis.

In general, experiments are carried out with Sod2CJE (−/−) mice, starting at 3 days of age, and the mice are weighed and divided into test and control groups. Test mice receive the compound for which evaluation as an antioxidant is desired at a dosage which is below the level of toxicity. Unless otherwise indicated, the test compound is administered in a pharmaceutically acceptable carrier by the intraperitoneal route. Unless otherwise determined to be advantageous, the test compound is administered at the same time each day (±2 hours).

During the course of an experiment, each mouse is evaluated daily for weight, lethargy, lack of appetite, its vital signs and for any indication of neurological disorders (observed for circling behavior, dystonia, trembling or the like. Video records can be made for later evaluation, for example for side-by-side comparisons or for observing changes over time. Cardiac histopathology and central nervous system tissue analysis are carried out after death of the animal or after sacrifice of the animal.

While the experiments with MnTBAP indicated that there was insufficient transmission of orally administered MnTBAP to the milk of nursing mothers, the ordinary skilled artisan understands that other routes of administration may be preferable or may facilitate experimental procedures for other potential MnSOD mimetics or antioxidants tested in the present animal model system. The skilled artisan understands how to test a particular compound for its toxicity in a particular mammal, for its ability to cross the blood-brain barrier and for its ability to enter the bloodstream and/or the cerebrospinal fluid. Preferred compounds are those which readily enter circulation and the central nervous system so that maximum amelioration of any disorder or disease resulting from oxidative damage, especially from superoxide radical.

TABLE 1

| MnTBAP | Litter Size | Median | Mean Lifespan | SD | N | P (Gehan's Wilcoxon test) |
|---|---|---|---|---|---|---|
| − | all | 8 | 8.3 | 4.4 | 94 | — |
| + | all | 20 | 16.4 | 5.8 | 31 | <0.000001 |
| − | Large | 5 | 6.5 | 2.9 | 59 | — |
| + | Large | 21 | 16.1 | 6.6 | 16 | <0.00002 |
| − | Small | 11 | 11.4 | 4.8 | 35 | — |
| + | Small | 19 | 16.6 | 4.9 | 15 | <0.007 |

TABLE 2

| | Age | | Lipid | | |
|---|---|---|---|---|---|
| | (Days old) | % Control | Mean | Mode | n |
| *Sod2$^{CJ3}$(−/−) | 6–10 | 100 | 4 | 4 | 5 |
| Sod2(+/+) | 12 | 0 | 0 | 0 | 3 |
| Sod2$^{CJE}$(−/−) | 12 | 23 | 0.9 | 0 | 9 |
| Sod2(+/+) | 14 | 6 | 0.25 | 0.5 | 4 |
| Sod2$^{CJE}$(−/−) | 14 | 23 | 0.9 | 0.5 | 8 |
| Sod2(+/+) | 17 | 38 | 1.5 | 2 | 4 |
| Sod2$^{CJE}$(−/−) | 17 | 40 | 1.6 | 2 | 8 |

TABLE 3

Induction of apoptotic messages in brainstem of SOD2−/− relative to Wild-type

| Genes | 12 days | 14 days | 17 days |
|---|---|---|---|
| Bcl-W | 25% | NS | NS |
| FLICE | 13% | NS | NS |
| Bfl-1 | 22% | NS | NS |
| Bcl-X | 15% | NS | NS |
| 0.05 > P > 0.004 | | | |

NS = not significantly different.
Message levels of Bak, Bax, Bcl-2, Bad, FAF, TNFRp55, FAS, FADD, and FAP were also evaluated and found to be not significantly different between treated wild-types and treated SOD2−/− at these three ages in the brain stem.

TABLE 4

Life spans of SOD2−/− mice treated with free radical scavenging compounds

| | Mean Lifespan (Days old) | SD | N |
|---|---|---|---|
| Untreated | 7 | 2.9 | 60 |
| Euk 8 | 22 | 8.5 | 25 |
| MnTBAP | 14 | 5.6 | 37 |

What is claimed is:

1. A method for identifying in vivo antioxidant activity of a compound, said method comprising the steps of:
   (a) providing a first homozygous transgenic mouse in which the genes encoding Manganese Superoxide Dismutase (MnSOD) have been inactivated;
   (b) providing a second homozygous transgenic mouse in which the genes encoding Manoanese Superoxide Dismutase (MnSOD) have been inactivated of the same age as the first homozygous mouse;
   (c) administering the compound to said first mouse only;
   (d) determining lifespans of the first and second mice; and
   (e) identifying a in vivo antioxidant activity of the compound where the lifespan of the first mouse to which the compound has been administered is longer than that of the second mouse to which the compound has not been administered.

2. The method of claim 1 wherein said homozygous transgenic mouse is a Sod2CJE(−/−) or a Sod2m1BCM(−/−) mouse.

3. The method of claim 2 wherein the homozygous transgenic mice are about 3 days of age when the compound is first administered.

* * * * *